United States Patent
VanSickle et al.

(10) Patent No.: US 8,594,778 B2
(45) Date of Patent: Nov. 26, 2013

(54) ACTIVE INVASIVE EEG DEVICE AND TECHNIQUE

(75) Inventors: David P. VanSickle, Denver, CO (US); Ken R. Winston, Golden, CO (US)

(73) Assignee: Regents of the University of Colorado, Boulder, CO (US)

( * ) Notice: Subject to any disclaimer, the term of this patent is extended or adjusted under 35 U.S.C. 154(b) by 1897 days.

(21) Appl. No.: 10/581,135

(22) PCT Filed: Dec. 17, 2004

(86) PCT No.: PCT/US2004/042488
§ 371 (c)(1),
(2), (4) Date: Apr. 3, 2007

(87) PCT Pub. No.: WO2005/058145
PCT Pub. Date: Jun. 30, 2005

(65) Prior Publication Data
US 2007/0265543 A1 Nov. 15, 2007

Related U.S. Application Data

(60) Provisional application No. 60/530,696, filed on Dec. 17, 2003.

(51) Int. Cl.
*A61B 5/04* (2006.01)
(52) U.S. Cl.
USPC .......................................................... 600/544
(58) Field of Classification Search
USPC .................................. 600/372, 382, 383, 544
See application file for complete search history.

(56) References Cited

U.S. PATENT DOCUMENTS

| | | | | |
|---|---|---|---|---|
| 5,281,221 | A * | 1/1994 | Tadych | 606/53 |
| 6,298,255 | B1 * | 10/2001 | Cordero et al. | 600/372 |
| 6,416,471 | B1 * | 7/2002 | Kumar et al. | 600/300 |
| 6,445,940 | B1 * | 9/2002 | Gevins et al. | 600/382 |
| 6,483,044 | B1 * | 11/2002 | Ahmad | 174/262 |
| 6,544,206 | B1 * | 4/2003 | Johnston, Jr. | 604/4.01 |
| 7,003,127 | B1 * | 2/2006 | Sjursen et al. | 381/322 |
| 2003/0004428 | A1 * | 1/2003 | Pless et al. | 600/544 |
| 2003/0125616 | A1 * | 7/2003 | Black et al. | 600/407 |
| 2003/0130585 | A1 * | 7/2003 | Wenger | 600/509 |

* cited by examiner

*Primary Examiner* — Navin Natnithithadha
*Assistant Examiner* — Etsub Berhanu
(74) *Attorney, Agent, or Firm* — Valauskas Corder LLC

(57) ABSTRACT

An electrode device for taking a plurality of EEG measurements, and an associated method of taking EEG measurements, whereby a plurality of electrode contact-points configured atop a support member are in electrical communication with, and in relative proximity to, an integrated circuit comprising converter circuitry adapted for converting analog EEG signals measured, having originated from within a patient, into digital signals prior to transmission thereof to a processing unit. The integrated circuit/circuitry (IC) may be supported by the support member or by a lead assembly having wiring for the digital signal transmission. The support member may have a plurality of layers and be generally flexible; as fabricated of any of a number of flexible, generally insulative biocompatible materials to which circuitry may be etched or deposited, exhibiting sufficient structural integrity to decrease likelihood of degradation during surgery or once implanted.

13 Claims, 4 Drawing Sheets

ACTIVE INVASIVE EEG DEVICE AND TECHNIQUE

CROSS REFERENCE TO RELATED PATENTS

This application claims the benefit of U.S. Provisional Application No. 60/530,696 filed Dec. 17, 2003 and International Application No. PCT/US2004/042488 filed Dec. 17, 2004.

BACKGROUND OF THE INVENTION

The present invention relates to electrodes used in taking invasive electrical encephalography (EEG, or electrocorticogram, EcOG) measurement(s). These EEG electrodes are often lumped into two general types, those using surface electrodes and those using depth electrodes.

Epilepsy is a neurological disorder characterized by the occurrence of seizures, specifically episodic impairment or loss of consciousness, abnormal motor phenomena, psychic or sensory disturbances, or the perturbation of the autonomic nervous system. Between 0.5% and 1.0% of the population suffers from epilepsy with approximately 20% having their disease poorly controlled by medications alone. Because epilepsy is characterized by seizures, its sufferers are often limited in the kinds of activities in which they may participate. Depending upon severity of seizures, epilepsy can prevent an individual from driving a vehicle, as well as performing other routine tasks. Some epilepsy sufferers have serious seizures so frequently they may effectively become incapacitated.

Once diagnosed, current treatment modalities for neurological disorders, particularly epilepsy, typically involve drug therapy and/or surgery therapy. While neurologists often turn first to treating epilepsy with drug therapy, the drugs used are not without serious side effects and high costs. Further, for many drugs, it is important to maintain a precise therapeutic serum level to avoid breakthrough seizures (if the dosage is too low) while minimizing toxic effects (dosage gets too high). Surgical approaches are based on the resection of a seizure focus. Implantable electrical stimulation of cranial nerves (especially cranial nerve XII) is also used for the treatment of epilepsy. While direct stimulation of neural tissue in the vicinity of a seizure focus is an emerging therapy for seizure control, the seizure detection capabilities of these systems is currently very limited.

Research on the detection of neurological conditions has focused on receipt and analysis of waveforms referred to in scientific literature as electroencephalogram (EEG) and electrocorticogram (ECoG) waveforms. In general, EEG signals represent aggregate neuronal activity potentials detectable via electrodes applied to a patient's scalp, and EcoG(s) use internal electrodes near the surface of the brain. Thus, ECoG signals, deep-brain counterparts to EEG signals, are detectable via electrodes implanted under scalp and cranium. Unless otherwise specified, "EEG" is used throughout to refer to both EEG and ECoG signals.

This invention is directed to a unique multifunctional Active-Invasive EEG device/system and associated technique comprising one or more surface and/or implantable electrodes—whether depth electrodes, cortical electrodes (subdural), or epidural electrodes. As further explained by applicants in their provisional application No. 60/530,696 (fully incorporated herein by reference) and in the instant disclosure, for simplicity and illustrative purposes, surface-recording electrodes are showcased herein, however within the spirit and scope hereof, depth-, epidural-, subdural-, and so on, type electrodes are contemplated. While the focus hereof is on epileptic disorders, the device/system and technique of the invention is useful for any of a wide variety of neurological disorders experienced by human and non-human/veterinary patients.

The electrode device and associated method of taking EEG measurements according to the invention comprises a plurality of electrode contact-points configured atop a support member. These contact-points are in electrical communication with an integrated circuitry/circuit ("IC" or "chip") that has converter circuitry adapted for converting analog EEG signals measured—having originated from within a patient—into digital signals. The integrated circuitry is also in electrical communication with a lead assembly that comprises wiring for electrical transmission of the digital signals. The IC is preferably either supported by the support member or this IC is located within the lead assembly slightly 'downstream' of the support member, permitting by-and-large "in-situ" processing (e.g., conversion to digital signals) of at least a portion of the analog EEG signals measured from within the patient. The conductive electrode contact-points may contact patient tissue on the surface, epidural, subdural, and so on, for taking the invasive EEG measurements depending upon the specific diagnostic EEG technique employed and associated locale of electrode device.

Neurosurgeons and neurologists may use the instant invention in treating patients with intractable seizures to complement and provide an optimal surgical management. For example, while a patient who suffers from seizures might be treated with surgical resection based on magnetic resonance imaging (MRI) or other imaging evidence alone, a significant fraction will likely additionally require either subdural or depth electrode monitoring for preoperative planning.

A conventional surface strip electrode is diagrammed in FIG. 1: This electrode device (2) has a single row of six electrical contact-points (5) embedded in a silastic matrix (7), each electrode point (5) has an individual wire (6). While six contacts are shown, any number of contacts can and have been implemented. These wires are bundled together (one wire per electrical contact-point) and electrically hardwired to connect to a respective individual contact (9) on a lead/cable. U.S. Pat. No. 6,597,954 B1, FIG. 2, depicts a device 110 having been intracranially implanted and affixed in a patient's cranium 214; the device 110 has a lead connector 220 adapted to receive electrical leads such as that at 222 (which is situated on the outer surface of the cranium 214 under the patient's scalp 112). The six electrode points (5) labeled in FIG. 1 hereof, are conductive for contacting patient tissue (not shown, for simplicity). The bundled leads penetrate out of the skin (for example, see FIG. 11 of U.S. Pat. No. 6,024,702 issued 15 Feb. 2000, where grid electrode 10—such as that in FIG. 5 and FIG. 10—is depicted used as a subdural electrode having been inserted between the brain surface labeled S and the dura labeled D). The several bundled leads are hardwire-connected to a recording machine/unit typically located some distance away from the patient. While invasive electroencephalogram (EEG) using conventional electrodes and associated monitoring units is a commonly used technique for surgical planning, the equipment currently available is cumbersome and monitoring requires expensive in-hospital stays.

To determine if a particular individual with uncontrolled epilepsy is a surgical candidate, two fundamental areas of cerebral cortex must be distinguished, the seizure focus (or foci) and any adjacent eloquent cortex. The seizure focus is that area of cortex where seizures originate(s) and is often abnormal. Surgical resections of a patient's brain are planned and carried out by a surgeon so as to not lead to worsening of neurologic function. Eloquent cortex areas are those areas of brain tissue that control 'critical functions' whereby surgical resection of the area would leave a patient impaired. These areas include, but are not limited to, Broca's and Werneke's area that control speech and the motor and sensory strips located in the pre-central and post-central gyri, respectively. While these areas are known anatomically, there is a significant amount of variability between individuals and these functional areas may have been remapped to other anatomical areas due to years of seizure activity. Therefore it is extremely important to have diagnosis tools that aid in accurately identifying those sections of the brain that ought to be removed, if at all.

Multiple techniques have evolved for the localization of the seizure focus and associated eloquent cortex including well-known imaging techniques employing PET and MRI scanners and the use of both invasive and scalp EEG recordings (EEG signals measured represent aggregate neuronal activity potentials detectable via electrodes applied to a patient's scalp or deeper from within). While imaging techniques have the advantage of being non-invasive, not all seizure foci can be determined even with the best available technology. And while useful under certain circumstance, scalp EEG data is not as effective or consistent at lateralizing even the most common surgically treated epilepsy of the temporal lobe. In cases where the seizure focus cannot be determined through imaging, most authorities now recommend invasive EEG monitoring usually taking place in an inpatient video EEG monitoring unit. For seizures related to errors in brain development, invasive EEG is almost always required due to the unpredictability of the seizure focus and eloquent cortex.

The invention described herein is a much improved invasive EEG monitoring system (ActiveInvasive EEG) allowing increased convenience—whether for shorter, outpatient monitoring or prolonged monitoring over an extended period—more accurate data, as well as offering a wider range of applications for invasively monitoring of brain activity and treating neurological disorders (such as epilepsy), for the neurosurgeon, neurologist, associated highly trained medical technicians, and human or veterinary patients. In connection with surgical/preoperative planning done by neurosurgeons and neurologists, the implantable ActiveInvasive EEG device with its design focused at collecting and converting analog signals originating from within the patient's brain nearer to the site of collection, provides the ability for long-term recording and surgical planning, as well as a providing a source of electrical stimulation in treatment of seizures. The implantable ActiveInvasive EEG device, thus, gives neurosurgeons and neurologists another powerful tool for use in surgical planning, treatment, as well as in designing flexible strategies for outpatient monitoring that employs this new EEG device.

Additional BACKGROUND TECHNOLOGY:
Provided by Way of Reference, Only

I. Microelectronics—Structures and Devices. Microelectronics is that area of electronics technology associated with the fabrication of electronic systems or subsystems using extremely small (microcircuit-level) components. Semiconductor fabrication and processing is driven by the computer-electronics industry. The demand for greater capability and faster data collection and processing drives demand for smaller-and -smaller integrated circuit (IC) microcircuits. "Chip" and/or 'microchip' are often used to refer to any one or interrelated operational set of micro-miniaturized, electronic circuits, or microdevices—including microprocessors—that have been designed for use as electrical components, processors, computer memory, as well as special purpose uses in consumer and industrial products; larger sized similarly-styled structures on the order of 1 cm and up, may also be referred to as 'chip'. The terms chip, integrated circuitry/circuit (IC), and microchip are often used interchangeably within the electronics industry: the smaller microchips can hold a handful to tens-of-thousands of transistor/electrical devices (chips of around $\frac{1}{16}$" square by $\frac{1}{30}$" thick); whereas larger-sized microchips sized on the order of $\frac{1}{2}$-inch$^2$, are capable of containing many millions of transistor/electrical devices. Generally, the top one-thousandth of an inch of a chip's surface holds the microcircuits, and the substrate below provides mechanical strength and stability. Microcircuit wafer fabrication generally starts with a substrate to which layers, films, and coatings (such as photoresist) can be added or created, and from which these added or created materials can be subtractively etched (for example, as in dry etching).

II. Digital computers. A processor is the set of logic devices/circuitry that responds to and processes instructions to drive a computerized device. The central processing unit (CPU) is considered the computing part of a digital or other type of computerized system. Often referred to simply as a processor, a CPU is made up of the control unit, program sequencer, and an arithmetic logic unit (ALU)—a high-speed circuit that does calculating and comparing. Numbers are transferred from memory into the ALU for calculation, and the results are sent back into memory. Alphanumeric data is sent from memory into the ALU for comparing. The CPUs of a computer may be contained on a 'chip', often referred to as microprocessor because of its tiny physical size. As is well known, the basic elements of a simple computer include CPU, clock and main memory; whereas a complete computer system requires the addition of control units, input, output and storage devices, as well as an operating system. The tiny devices referred to as 'microprocessors' typically contain the processing components of a CPU as integrated circuitry, along with associated bus interface. A microcontroller typically incorporates one or more microprocessor, memory, and I/O circuits packaged as an IC. Computer instruction(s) are used to trigger computations carried out by the CPU.

III. Computer Memory and Computer Readable Storage. While the word 'memory' has historically referred to that which is stored temporarily, with storage traditionally used to refer to a semi-permanent or permanent holding place for digital data—such as that entered by a user for holding long term—more-recently, the definitions of these terms have blurred. A non-exhaustive list of well known computer readable storage device technologies are categorized here for reference: (1) magetic tape technologies; (2) magnetic disk technologies include floppy disk/diskettes, fixed hard disks (found in desktops, laptops, workstations, etc.), (3) solid-state disk (SSD) technology including DRAM and 'flash memory'; and (4) optical disk technology, including mag-neto-optical disks, PD, CD-ROM, CD-R, CD-RW, DVD-ROM, DVD-R, DVD-RAM, holographic, solid state optical disk technology, and so on.

SUMMARY OF THE INVENTION

It is a primary object of the invention to provide an electrode device for taking a plurality of EEG measurements, and an associated method of taking EEG measurements, whereby a plurality of electrode contact-points configured atop a support member are in electrical communication with, and in relative proximity to, an integrated circuit comprising converter circuitry adapted for converting analog EEG signals measured, having originated from within a patient, into digital signals prior to transmission thereof to a processing unit. The integrated circuit/circuitry (IC) may be supported directly by the support member or in proximity thereto and by a lead assembly connected to the contact points that has wiring for the digital signal transmission. The plurality of electrode contact-points preferably contact tissue of a patient (where this contact occurs, depends upon the type of lead: e.g., surface, subdural, epidural, etc.) to obtain measurements originating within the patient.

There are numerous further distinguishing features of the electrode device and associated method of the invention: The support member may comprise a plurality of layers, including a power plane and a ground reference plane to reduce interference fro electromagnetic noise. The support member may be generally flexible; it may be fabricated of any of a number of flexible, generally insulative biocompatible materials to which circuitry may be etched or deposited, exhibiting sufficient structural integrity to decrease likelihood of degradation during surgery or once implanted. The IC further comprises circuitry for digital filtering and signal analysis of the digital signals, as well as memory for storing/holding the processed digital signal information. The IC will also have facilities for the electrical stimulation of cortex or other neural structures through any preselected combination of contact-points. Lastly, the IC preferably also has the ability to coalese the digital signals by the use of a bus protocol (e.g. Ethernet), significantly reducing the number of wires and external contacts required. A quick-connect mechanism located along the lead assembly between the IC and a host processing unit, an antibiotic cuff mechanism located along the lead assembly between the quick-connect mechanism and the patient (to aid in preventing infection), as well as a stabilizer of the lead assembly to a location on the patient (e.g., surgically affixed to the patient's scalp) to aid in maintaining the electrode assembly in place, may also be included. Specifically the IC may further include circuitry for: (a) digital filtering of the digital signals; (b) signal analysis and processing of the digital signals; (c) memory storage of the processed digital signals; (d) electrical stimulation of cortex or other neural structures, (e) coalescing the digital signals employing suitable bus protocol, reducing total number of external wiring and contacts; and (f) wired or wireless transmission outwardly from the patient, of electromagnetic signals comprising information about the processed digital signals.

The digital signals from the IC are received by a processing unit which has the capacity to store (in memory), further digitally process and/or transmit the data to a host unit. The transmission may be performed either through wired or wireless means. The processing unit may consist either of an external recorder-processor unit worn by, or proximate to, the patient and physically connected through the lead assembly through an antibiotic cuff or may be implanted into soft tissue for a system entirely implanted with no external connections. The host unit is used for display, further processing, analysis and storage of the unprocessed or processed EEG data. In another embodiment of the device, a combination of the processing and host unit is contemplated. A quick-connect mechanism may be disposed along the cabling between the IC-lead assembly and the processing unit (recorder-processor unit and/or central processing area) where cabling/hardwiring is employed.

In another aspect of the invention, a separation marking between at least one of the contact-points and a second of the contact-points is included; this permits a severing of the support member there along for removing a portion of the support member containing one or more contact-point that is not needed during monitoring. A remaining portion of the support member comprising the IC is then used for measuring analog EEG signals originating from the patient through the remaining electrode contact-points. A similar separation may also be used to separate electrically connected groups of grid or strip electrodes to eliminate the need for internal connectors.

As can and will be appreciated, certain of the many unique features, as well as the further-unique combinations thereof, supported and contemplated hereby within the spirit and scope of this disclosure, may provide a variety of advantages. The advantages of the new features and combinations disclosed herein will be appreciated, especially by providers of medical and veterinary neurological care/services and products, by perusing the instant technical discussion, including drawings, claims, and abstract, in light of drawbacks to traditional devices identified herethroughout, or as may be uncovered.

BRIEF DESCTIPTION OF THE DRAWINGS

For purposes of illustrating the innovative nature plus the flexibility of design and versatility of preferred and alternative electrode device and associated method of taking a plurality of EEG measurements, supported and disclosed hereby, the invention will be better appreciated by reviewing accompanying drawings (in which like numerals, if used, designate like or similar parts). One will appreciate the features that distinguish the instant invention from conventional structures. The drawings have been included to communicate the innovative core structure and further unique features of the device and associated method, as well as to demonstrate the unique approach taken, by way of example only, and are in no way intended to unduly limit the disclosure hereof.

FIG. 1 is a diagram of conventional surface strip electrode device 2.

FIG. 2 diagrammatically represents, as a top plan view, an embodiment of a new electrode device for taking EEG measurements according to the invention.

FIG. 3A diagrammatically represents an example-alternative embodiment of an electrode device having an array of contact-points and IC elements paired therewith.

FIG. 3B diagrammatically represents yet another alternative electrode device initially fabricated such that contact-point IC pairings may be separated along 65b.

FIG. 4 diagrammatically represents yet another embodiment of an electrode device whereby the IC element (20a) is located 'downstream' along the lead assembly.

FIG. 5 diagrammatically represents a quick-connect mechanism whereby a processing unit (not shown) may be interconnected with a lead assembly.

DETAILED DESCRIPTION OF EMBODIMENTS IN DRAWINGS

Figure 1:
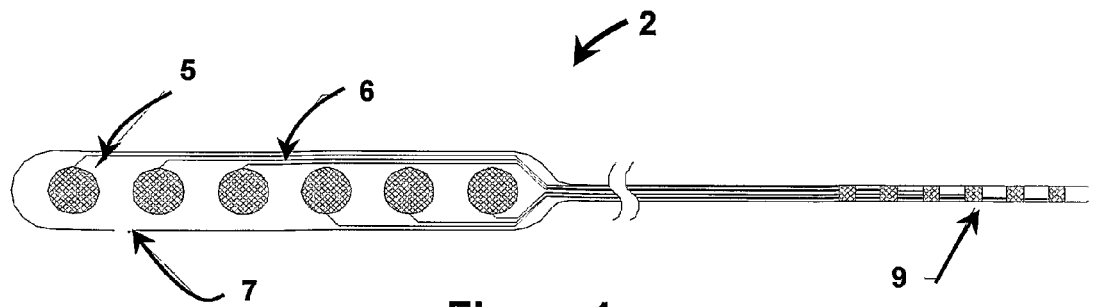

The novel multifunctional compact electrode device, system and technique is employed for the collection of information in the form of EEG waveforms from the brain of any animal (including humans as well as domesticated farm and ranch animals, pets, etc., and those in the wild) in connection with the detection, monitoring, and treatment of neurological disorders, particularly epilepsy, which is often progressive and can lead to deterioration of other brain functions as well as physical impairment(s). Reference is made back-and-fourth to FIGS. 2-7, in discussing features of the various embodiments.

As mentioned, neurosurgeons and neurologists may use one or more electrode device of the invention in treating patients with intractable seizures to provide an optimal medical management. It is estimated that between 0.5 and 1.0% of the human population have seizures, with ~20% of these not properly controlled with medications, alone. Many of these individuals might be treated using MRI or other imaging evidence alone; however, a significant fraction likely require either subdural, epidural or depth electrode monitoring for preoperative planning. The electrode devices of the invention each comprise one or more chips with a minimal number of supporting components, including fabrication by embedding the IC into a silastic membrane supporting electrode contact-points configured in an array/grid or along a strip. Electrode contact-points, leads, and output contacts are fabricated from known conductive materials.

In addition to reducing costs by providing a means by which monitoring for seizures may be accomplished as an outpatient or in an inpatient setting, the novel electrode devices of the invention may be left in place for extended periods of time. This flexibility of use further permits a greater number of patients to be monitored and undergo treatment. For example, a patient may have seizures that are uncontrolled by medications, but simply not frequent enough to be reliably measured during a limited one to two week in-hospital stay. One example is a patient with multiple seizure foci that can be controlled with minimal medical therapy, but one or more foci which is/are uncontrolled. This patient would not be offered surgery due to the multifocal nature of his disease. However, by leaving one or more electrode devices of the invention implanted, or otherwise placed for collecting EEG data, for an extended period(s) of time, the medications can be systematically adjusted revealing just which areas of the cortex would be amenable to surgery and which should be left intact and treated medically. The ability to implant and leave the electrode device of the invention in place for a longer period of time, whether in an inpatient or outpatient setting, permits the use of focused radiosurgery for seizure foci ablation instead of the use of open surgical techniques, as is currently done. Preferably, an electrode device is implanted and the seizure focus/foci identified after appropriate systematic adjustment of the patient's medications has been done. Thereafter, a specific focus or multiple foci may be treated using radiosurgery. The electrode device may remain in place to monitor and confirm that a patient's seizures are under control. Multiple radiosurgery sessions would be possible allowing for conservative initial treatment. After the seizures have been controlled as documented by implanted electrode devices of the invention, the electrodes may be removed. Another example is to employ the novel devices to perform detection functionalities in a seizure termination device such as those using electrical stimulation, cold, or drug therapy as a treatment modality.

The unique ActiveInvasive EEG of the invention comprises a combination of mechanical and functional enhancements for use as an invasive EEG modality, these include: (A) The incorporation directly with the support member or in proximity thereto and supported by the lead assembly, of an IC containing circuitry for providing certain functionalities 'on-site' of obtaining EEG signals: 1) Analog signal conditioning, 2) Analog filtering, 3) Analog-to-digital conversion, 4) Signal integration from multiple grid or strip electrodes, 5) Digital filtering and processing (pre-processing), 6) Digital signal analysis, 7) Electrical stimulation of tissue as a treatment modality, 8) coalescence of digital signals through a bus protocol (e.g., Ethernet), 9) Digital data computation and transmission (e.g., wireless transmission), and 10) Temporary storage/memory of data. (B) The incorporation of: at least one signal bus for transmitting signals over wiring using a transmission protocol such as the stochastic based Ethernet protocol; a quick-connect assembly; use of a multi-layered support member having power and ground planes for improved signal fidelity; and an implantable recording/storage device for EEG information and wireless transmission of EEG data to a remote receiving-unit.

Figure 2:
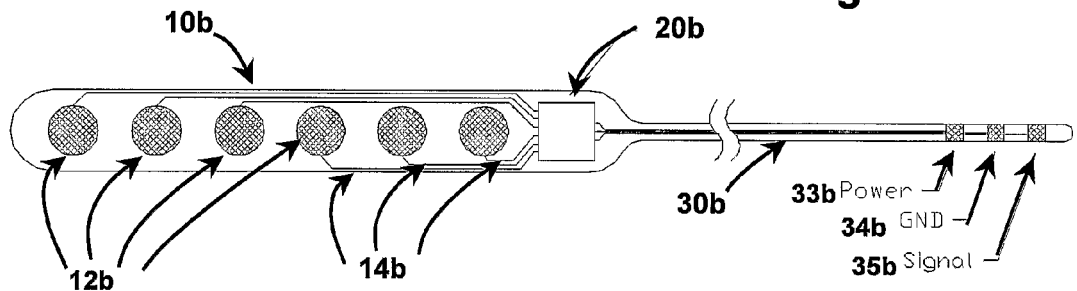

The strip electrode 100b depicted in FIG. 2 includes a 1×6 array of electrode contact-points 12b, each of which has a dedicated lead/wire 14b in electrical communication with an IC 20b, from which lead assembly 30b extends. For this six-position/point strip electrode, the number of external contacts along lead 30b has been reduced to three, 33b, 34b, 35b. By performing analog-to-digital signal conversion 'on-site' closer to the source of collection, signal-to-noise ratio is much improved.

Figure 3A:
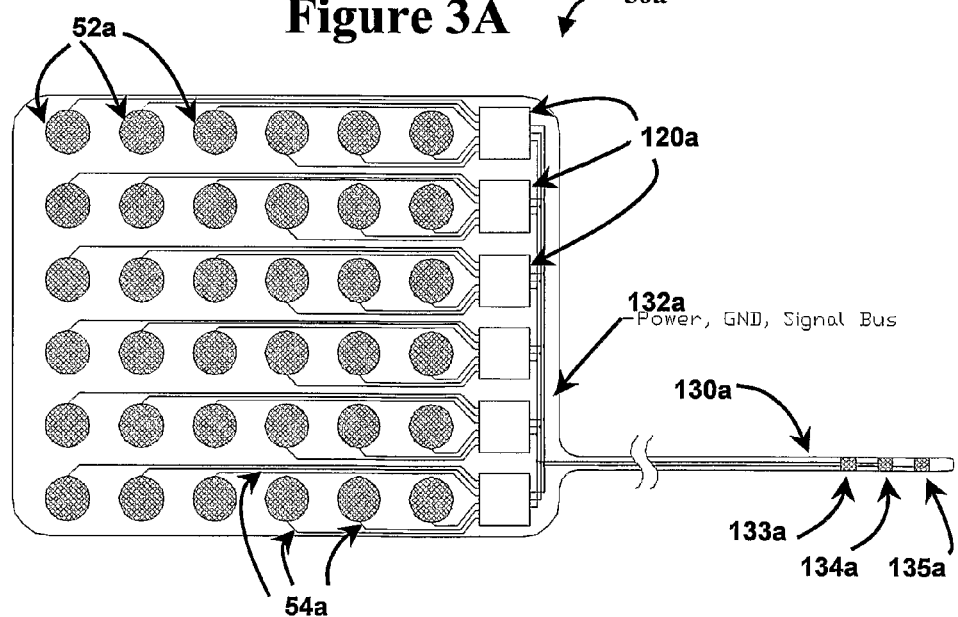
Figure 3B:
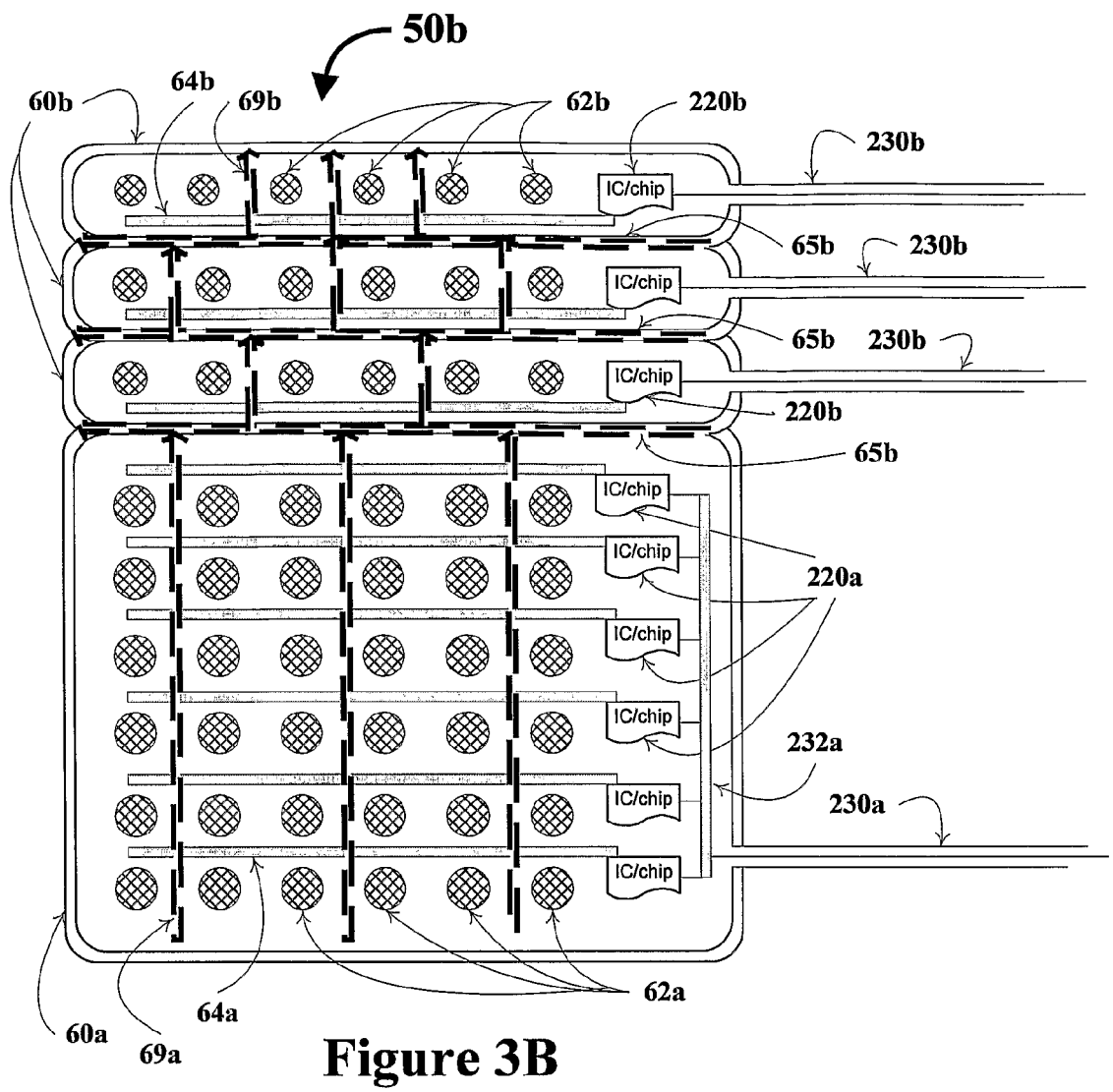

Additional strips and associated electrode contact-points can be interconnected while only requiring three output contacts (Power, GND, signal at 33b-35b and 133a-135a) for operation, see also FIGS. 3A-3B. Thus, whether or not the total number of electrode contact-points is increased within the electrode device, only three output contacts are required (e.g., 33b, 34b, 35b) providing a significant advantage.

Analog-to-digital conversion closer to the source of analog signal collection at or within brain tissue markedly improves signal-to-noise ratio. The device (e.g., at 100a, 100b, 50a, 50b) has significantly greater 'immunity' to noise from external sources of radiation such as sixty-cycle power transmission, radio broadcasts, and so on, that can affect readings. Digital filtering and signal analysis provides greater flexibility than working with analog signals. Digital filtering reduces cost and complexity of the circuitry, due in part because many of the functions that can be performed effectively digitally, would require costly precision analog components.

Analog signal condition consists of signal amplification and appropriate scaling for later conversion to a digital signal. Analog filtering is necessary for analog-to-digital conversion to prevent aliasing where a higher frequency signal is interpreted as a lower frequency signal due to limitations based on the rate at which samples are recorded. The Nyquist criteria states that signals must sampled at twice the rate of the highest frequency in order that they be faithfully represented as a digital sequence. Since all real signals contain an infinite spectrum, the higher frequencies should be limited with analog low-pass prior to sampling. In practice, signals are acquired at a multiple of the Nyquist specified rate due to the limitations of analog filtering.

Note that, according to the invention, data/information collected from animal tissue (FIG. 7 at 210A, 210B) at the various electrode contact-points may be transmitted toward a central processing area 90 away from the patient on a single wire/cable/lead assembly (FIGS. 2, 3A, 3B, 4, and FIG. 7 at 30a, 30b, 130a, 230a, 230b). With the use of suitable protocol for data transmission, the digital signals converted from analog signals measured using one or more of the implanted electrode strips are transmitted to a central/host processing unit (90, FIG. 7) through a recorder -processor unit 60 or directly (50) from the IC/chip/lead assembly 20a/30a. Once again, only three output contacts (33a-35a, 33b-35c, 133a-

135*a*) may be used regardless of total number of contact-points (12*a*, 12*b*, 52*a*, 62*a*, 62*b*) utilized to collect data. While, it may be desirable to increase the number of output contacts for technical improvement, one /benefit of the core invention is an ability to reduce total (sets) of output contacts that carry data/info collected, away from patient to central processing area.

FIG. 3A depicts a 6×6 grid device 50*a*. The use of one or multiple IC's 120*a*, with contact-point wiring 54*a* leading to an associated IC at the end of a 1×6 row, and combining outputs 123*a*—thus, requires only three external contacts 133*a*-135*a* and one lead assembly 130*a*. Were there no ICs (120*a*) in the 6×6 grid array, the device would become unduly complex and cumbersome to use as it would require up to six external leads, with an associated output contact for each lead, for each 1×6 row of contact -points 52*a*. The power, ground (GND), and signal connections from each of the six IC's (120*a*) are bussed together 132*a*. The total number of IC's shown in this diagram is six, however, based on IC fabrication technology considerations, fewer IC's may be needed in the event each of the IC used is adapted to comprise a greater number of analog inputs.

Figure 4:
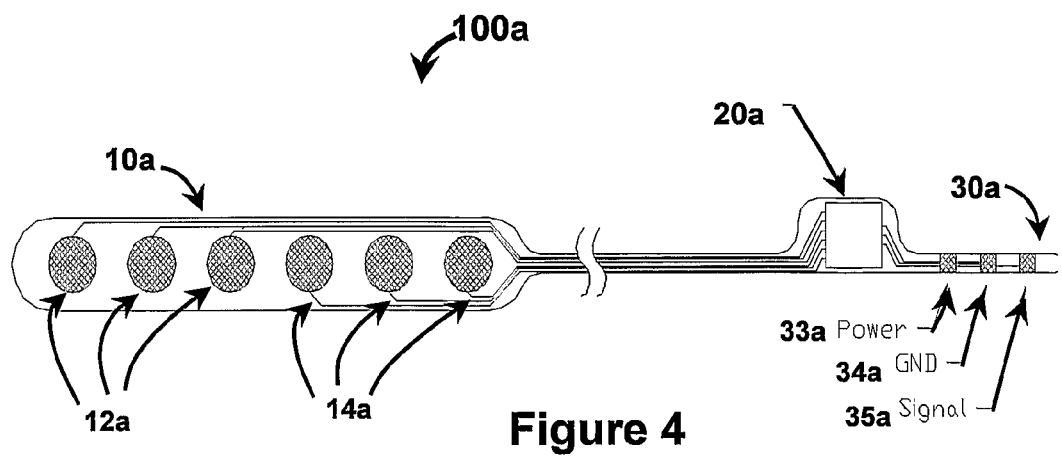
Figure 6:
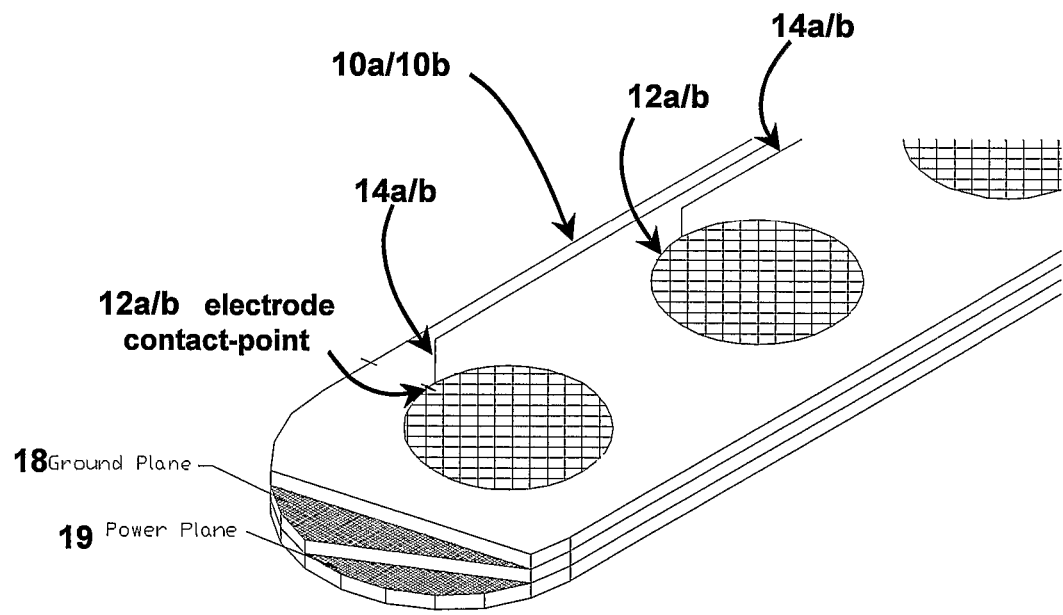
FIG. 6 is a isometric (partial view) of a distal end portion of an electrode device such as that depicted in either FIG. 2 or FIG. 4 whereby sections of a multi-layered support member have been cut-away for purposes of illustration.

As one can appreciate, the FIGS. 2 and 3A structures represents only a couple of the many suitable strip and grid configurations, respectively, of electrode points and associated IC functional units, contemplated according to the invention. For example, the electrode device may accommodate additional, or fewer IC's depending upon the number of analog inputs permitted each individual IC. The electrode contact-points are configured, for example as shown in FIGS. 3A-3B into an array/grid of rows, and incorporated into and atop a support member having a periphery of suitable shape (s) (for example, as shown in FIGS. 3A-3B the support member is rectangular in shape, while each support member 10*a*, 10*b* in FIGS. 2 & 4 are shaped as an elongated strip). The support member, as described further, is preferably multi-layered (FIG. 6, depicting a ground plane 18 and power plane 19 beneath a top layer of support member such as that throughout and labeled 10*a* or 10*b*).

An alternative embodiment of the invention is the use of multiple strips or grids grouped together either with or without connectors, either semi-permanently such as that in FIG. 3B whereby individual contact-points and/or wiring therefrom or groups of contact-points and associated wiring, may be severed along areas marked 65*b*, 69*a*/69*b* (further explained) or grouped together permanently to be used together for targeted detection of seizure activity or other tissue electrical activity. Electrically, these multiple grids (e.g., 50*a*, 60*a*) or strips (e.g., 10*a*, 10*b*, 60*b*) are ideally connected with the power, ground and signal in parallel so that the total number of external leads is one and the total number of external contacts is three. FIG. 3B depicts an expanded 9×6 grid structure that has logical groupings at 60*b* of three 1×6 rows of contact-points 62*b* associated with wiring/leads 64*b* and an IC 220*b* (similar to structure 10*b*, FIG. 2) and a 6×6 grouping 60*a* (similar to grid structure 50*a*, FIG. 3A) having six rows of 6 contact -points 62*a*, each 6 contact-points associated with wiring/leads 64*a* and a respective IC 220*a*. FIG. 3B depicts only one layout of logical groupings of contact-points 62*a*/62*b* and associated wiring 64*a*/64*b*, IC's 220*a*/220*b*, and lead assemblies 230*a*/230*b* that can be constructed to form a kit-style multi-grid device 50*b*. Additional separations such as those areas marked 65*b*, 69*a*/69*b* may be added. Markings include printed indicia or etching, embossing, or otherwise physically thinning the separation to make severing easier. Contact-points (62*a*/62*b*) and associated wiring/leads (64*a*/64*b*) may be clustered in alternative patterns (e.g., star-shaped, octagonal etc. rather than ordered in rows, as shown by way of example herein) with separations between patterns that permit severing therealong to remove unneeded contact-points, wiring, and support member 'real estate' prior to implanting, or otherwise locating, the support member for EEG monitoring.

The 1×6 strip electrode 100*a* in FIG. 4 depicts IC 20*a* in an alternate position: within the lead assembly 30*a*, yet in proximity to support member 10*a* for 'on-site' digital processing functions. The IC may be placed in a number of other positions on the strip electrode 10*a*. The placement of the IC along lead 30*a* may be selected where excess heat generation is a concern. Depending on total number of electrode points interconnected with the IC, how the IC is fabricated (materials, number of layers, etc.), total number of electrode strips, where the IC unit is located within the human or animal tissue, and so on, there may be too much thermal energy generated within and around one or more of the IC('s) during operation/use for the human or animal tissue to tolerate. Thus, location 20*a* of the IC unit is contemplated remote from the electrode contacts, as shown: The IC may be placed in the subdural space. Or, the IC may be placed under the scalp away from the cortical surface. The embodiment at 100*a* FIG. 4 has IC 20*a* built into the external lead/cable 30*a* allowing it to be placed above the bone flap, but below the scalp where the patient's body temperature is lower. Preferably, and according to the invention, one or more IC may also have additional functional capabilities to stimulate the brain. This allows for mapping of the eloquent areas of cortex and will provide a source of electrical stimulation in the treatment of seizures.

A "bus" in an electrical circuitry is defined, generally, as: One or more conductor (conductive leads/wiring) or optical fibers (where information is transmitted via optical signals) that serves as a common connection for a group of related electronic devices/components. Use of suitable protocol to transmit data digitally over a single wire/cabling (using a suitable ground) is another feature of the electrode device of the invention. Signal transmission protocols that allow for single wire transmission (allowing for a ground return path) of digital data, already exist. One example is the stochastic Ethernet protocol. The signal output contacts of each lead can be electrically connected together, as can the power and ground output contacts of each lead. With this ability, a system of 128 electrodes as part of both grids and strips implanted in a single patient would require only one external lead with three output contacts versus the minimum of 8 (assuming 16 contacts per lead) leads required with current, conventional invasive EEG systems.

Figure 5:
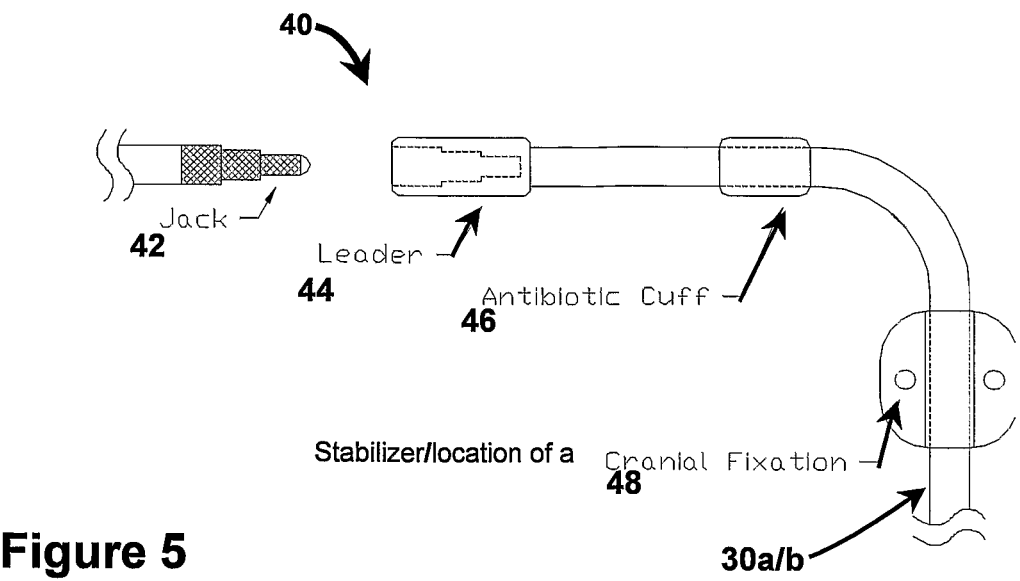
Figure 7:
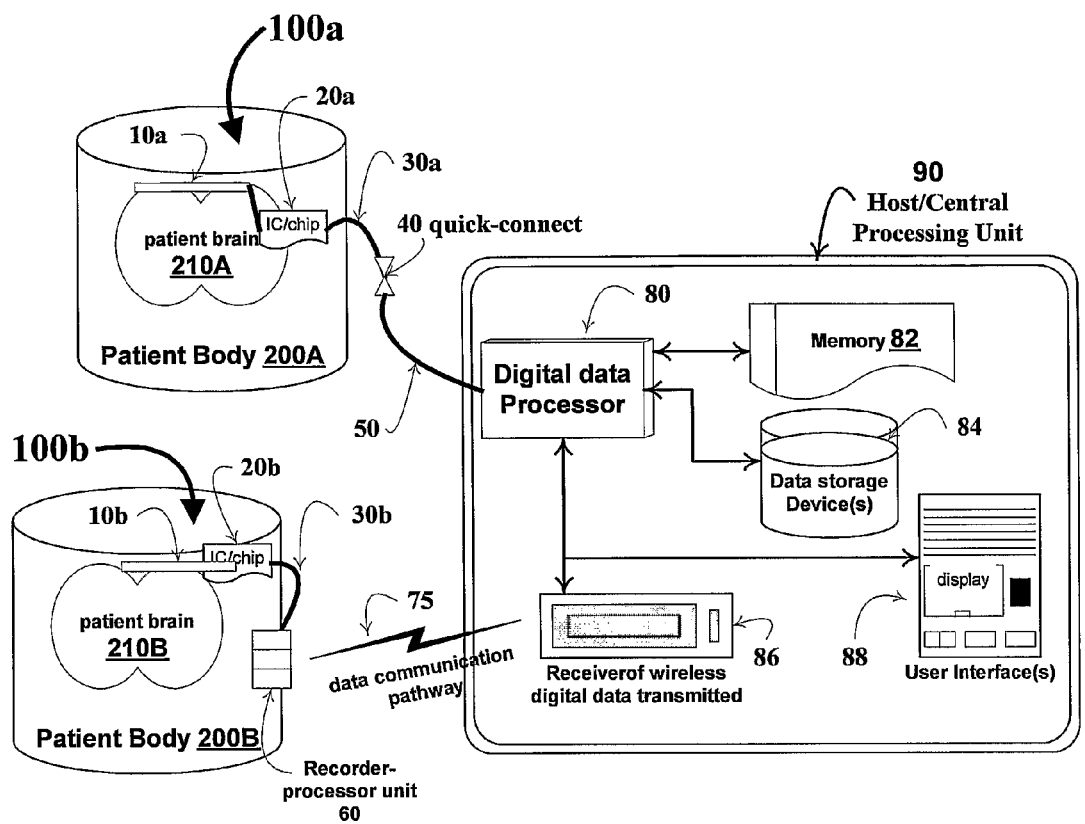
FIG. 7 is a schematic diagram representing features of an electrode device, system and technique/method of taking EEG measurements according to the invention; illustrated are core, as well as further distinguishing features, by way of example.

FIG. 5 depicts an embodiment of a quick-connect mechanism 40 having a three-conductor jack 42 insertable into a mating receptacle/receiving end 44. The receptacle 44 is attached to a lead assembly 30*a*/30*b* such as is shown in FIGS. 2, 4, 7 (as well as 130*a*, 230*a*, 230*b* in FIGS. 3A-3B) that, upon being implanted, is tunneled out through the scalp of a patient. Conventional invasive EEG electrode designs have leads connected to an external recording system that do not permit the patient undergoing in-hospital treatment to move very far during the monitoring period. Instead, and preferable, is an ability of the patient to move around the room without danger of pulling electrode grids or strips from their surgically implanted locations. A quick-connect mechanism having the proximal portion anchored to the skull with suitable fastener(s)—for example, as shown and labeled 'stabilizer' 48 in FIG. 5 (preferably attached at a suitable cranial fixation location)—is contemplated here. Suitable fasteners include screws similar in design to existing plating systems currently used for fixation of bone flaps created during craniotomy surgery.

An antibiotic cuff 46 is incorporated into the device as shown in FIG. 5, to prevent infection from traversing the tunnel and into the patient. If the patient, through normal movement or as part of a seizure, moves in a manner to cause strain on the external recording system, connector mechanism 40 will pull apart rather than having the strips of electrode points be dislodged. The quick-connect is designed such that the force required to pull-apart the jack and receiving end be sufficient to hold the mechanism together during monitoring and/or treatment, yet light enough to permit the mechanism to pull apart before the grids or strips of electrode contacts experience force enough to cause them to be displaced. During monitoring, in the event the connect mechanism is—whether due to seizure or other disturbance to the patient (e.g., the patient needs to use a rest room)—disconnected, the electrode device(s) implanted in the patient may simply be reconnected to the external recording unit/system in a 'snap'.

Printed circuit boards used in computerized devices are built with the capability to 'shun' interference due to external electromagnetic (EM) radiation from power lines, RF (radio freq) emissions, etc. As mentioned, EM signals/radiation can interfere with both surface and invasive EEG monitoring. The FIG. 6 cutaway illustrates an embodiment of a strip electrode device that has both power 19 and ground planes 19 incorporated within the support member 10*a*/10*b* made out of, for example, a silastic membrane/material. Power and ground planes provide EM shielding for the electrode contact-points. As depicted in FIG. 6, two planes made from electrically conductive material such as, but not limited to, silver built into the silastic membrane (or other flexible, non-conducting, biocompatible-type material) member 10*a*/10*b* supporting the electrode contact-points of the strip or grid electrodes. The support member is preferably multi-layered (at least one of which is conductive for purposes of EM shielding) and of suitable shape to accommodate a preselected electrode contact-point configuration.

For prolonged/extended use, it is preferable to have no external, hardwire cable connection extending the entire length from an implanted electrode device(s) to central processing area (90). An embodiment that is comprised of an implantable electrode device 100*b* (FIG. 7) that does not require full-length external cabling from the IC/lead assembly 20*b*/30*b* to central processing unit 90, is contemplated herein; e.g., electrode device 100*b*, FIG. 7 utilizes data communication pathway 75 between patient body 200B and central unit 90. While the alternative device at 100*b* depicts use of a recorder-processor unit 60 for wireless transmission 75 of processed digital signal information—having arrived through a lead assembly 30*b* of a length extending from IC unit 20*b* to the recorder-processor 60—as has been mentioned elsewhere herein (please refer to the SUMMARY OF THE INVENTION section), wireless transmission may instead be done using a lead assembly that comprises a short/tiny section of antenna wiring (significantly shorter than that depicted in FIG. 7 at 30*b*), such that EM waves are effectively transmitted from the region of IC 20*b*. In this case, a quick-connect 40 and cable 50 would not be required for communicating with central processing unit/area 90.

In the event that space in the subgalial compartment is insufficient to house an electrode device (100*a*, 100*b*, 50*a*, 50*b*) locations such as in axilla may be used, as has been done in the past successfully for devices such as the vagal nerve stimulator and the deep brain stimulator. Furthermore, tunneling techniques have already been devised and are in use for the routing of the leads for conventional invasive EEG devices. These tunneling techniques are, in turn, based on techniques for the placement of shunts for hydrocephalus. Placing an implantable recorder-processor unit—shown schematically quite large at 60 in FIG. 7—in the axilla or other convenient corporeal compartment, the output lead assembly comprising the three conductors (dedicated for power, ground, and signal, such as is shown in FIGS. 2-4) may be routed from the subgalial space under the subcutaneous tissue to the implantable recorder-processor unit, or to an externally worn (e.g., a hand-held sized unit) recorder-processor unit 60, FIG. 7. Note, once again, that a minimum of three conductors (power, ground, signal) is preferred, however, more or fewer than three conductors may be used according to the invention.

Recorder-processor unit 60 is adapted for receiving and storing the data collected and digitally converted, and for wireless transmission 75 (and/or alternatively, hardwired transmission) to a central processing area 90. As mentioned, depending upon its location—whether implanted—IC 20*b* may be further adapted to transmit wirelessly to unit 60, which can store and transmit 75 periodically as a downloading of a collection/compilation of processed digital data. While it may be desirable to include a small additional unit of circuitry (which, if size appropriately small, may be implanted) comprising a data storage device, power source (battery) and wireless transmission capability (antenna wiring) at a site remote from an electrode support member 10*a*/10*b*, using current microcircuit technology, the data storage, power source(s), and wireless EM data transmission capability(ies) may be built into one or more IC (e.g., 20*a*/20*b*, 120*a*, 220*a*/220*b*) of the device—which can be located on the electrode support member (e.g., 10*b* in FIG. 2, and FIGS. 3A-3B)—further reducing the total number of components. Note that the recorder-processor unit 60 may alternatively be worn by a patient 200B employing suitable, conventional systems of straps, belts, pockets, etc, (not shown, for simplicity). Electrode devices 10*a*/10*b*, 50*a*/50*b*, 100*a*/100*b*—since they are adapted for fabrication as disposable devices comprising electrode contact-points in selected configuration atop a support member—can aid in reducing overall cost of EEG monitoring capital equipment. The novel associated method of EEG monitoring—readily discernable in connection with the disclosure and technical discussion of novel structural features of the invention—may be used as a research tool for collecting valuable data/information permitting trained medical professionals to predict clinical seizure activity and, using that information, terminate seizure(s) electrically.

While certain representative embodiments and details of an example have been shown merely for the purpose of illustrating the unique electrode devices and associated technique/method of the invention, including any program code utilized to instruct electrode devices to operate and to carry out the method of taking EEG measurements according to the invention, those skilled in the art will readily appreciated that various modifications, whether specifically or expressly identified herein, may be made to any of the representative embodiments without departing from the novel teachings or scope of this technical disclosure. Accordingly, all such modifications are contemplated and intended to be included within the scope of the claims. Although the commonly employed preamble phrase "comprising the steps of" may be used herein in a method claim, applicants do not intend to invoke 35 U.S.C. §112 ¶6. Furthermore, in any claim that is filed herewith or hereafter, any means-plus-function clauses used, or later found to be present, are intended to cover at least all structure(s) described herein as performing the recited function and not only structural equivalents but also equivalent structures.

What is claimed is:

1. An electrode device for taking a plurality of EEG measurements, comprising:
   (a) a first plurality of electrode contact-points configured atop a support member, where said support member is generally flexible and comprises a plurality of layers;
   (b) said first plurality of electrode contact-points in electrical communication with, and in relative proximity to, a first integrated circuit comprising converter circuitry adapted for converting analog EEG signals measured, having originated from within a patient, into a first set of digital signals prior to transmission thereof to a processing unit;
   (c) said first integrated circuit in further electrical communication with a lead assembly having wiring for transmission of said first set of digital signals;
   (d) a second plurality of electrode contact-points configured atop said support member and in electrical communication with a second integrated circuit comprising converter circuitry adapted for converting analog EEG signals measured by said second plurality of electrode contact-points, into a second set of digital signals;
   (e) a separation marking between said second plurality of electrode contact-points in electrical communication with said second integrated circuit and said first plurality of electrode contact-points in electrical communication with said first integrated circuit, permitting a severing of said support member therealong;
   (f) a quick-connect mechanism located along said lead assembly between said first integrated circuit and said processing unit, said quick-connect mechanism adapted to pull-apart upon a disturbance by said patient; and
   (g) an antibiotic cuff mechanism located along said lead assembly between said quick-connect mechanism and a stabilizer of said lead assembly to a location on said patient.

2. The electrode device of claim 1 wherein:
   (a) said plurality of layers of said support member comprises a power plane of electrically conductive material and a ground reference plane; and
   (b) each said first integrated circuit and said second integrated circuit further comprises circuitry for digital filtering and signal analysis of said first set of digital signals and said second set of digital signals respectively.

3. The electrode device of claim 1 wherein each said first integrated circuit and said second integrated circuit further comprises circuitry for:
   (a) digital filtering of said first set of digital signals and said second set of digital signals;
   (b) signal analysis and processing of said first set of digital signals and said second set of digital signals to obtain a first set of processed digital signals and a second set of processed digital signals;
   (c) memory storage of said first set of processed digital signals and said second set of processed digital signals;
   (d) coalescing said first set of processed digital signals and said second set of processed digital signals employing a bus protocol for reducing wiring; and
   (e) wireless transmission of information about said first set of processed digital signals and said second set of processed digital signals.

4. The electrode device of claim 1 wherein each said first integrated circuit and said second integrated circuit further comprises circuitry for:
   (a) digital filtering and signal analysis of said first set of digital signals and said second set of digital signals; and
   (b) said processing unit comprises a recorder-processor unit for receiving information about said first set of digital signals and said second set of digital signals from either of said first integrated circuit and said second integrated circuit, said recorder-processor unit adapted to be worn by said patient, and a transmission medium disposed between either of said first integrated circuit and said second integrated circuit and said recorder-processor unit.

5. The electrode device of claim 4 wherein said transmission medium is selected from the group consisting of:
   (a) air, wherein said information is transmitted wirelessly, and
   (b) cabling, a first end of which is in electrical communication with either of said first integrated circuit and said second integrated circuit and a second end of which is connected to said recorder-processor unit.

6. The electrode device of claim 5 wherein said cabling further comprises the quick-connect mechanism located along said lead assembly between either of said first integrated circuit and said second integrated circuit and said recorder-processor unit, said quick-connect mechanism adapted to pull-apart upon a disturbance by said patient, and a host processor remotely located from said recorder-processor unit for further processing said information.

7. The electrode device of claim 1 wherein said processing unit further comprises:
   (a) a host processor remotely located from said support member; and
   (b) wherein each said first integrated circuit and said second integrated circuit is supported by said lead assembly, and said plurality of layers of said support member further comprises a power plane of electrically conductive material and a ground reference plane.

8. The electrode device of claim 1 wherein said separation marking is one or more selected from the group consisting of:
   printed indicia, etching, embossing, and a physical thinning for permitting a severing of said support member therealong for removing a portion of said support member containing at least one contact-point; and
   wherein a remaining portion of said support member comprises at least one of said first integrated circuit and said second integrated circuit used for measuring analog EEG signals through one of said first plurality of electrode contact-points and said second plurality of electrode contact-points of said remaining portion.

9. The electrode device of claim 1 further comprising:
   (a) said second integrated circuit in electrical communication with said lead assembly; and
   (b) said plurality of layers of said support member having a power plane of electrically conductive material and a ground reference plane.

10. A method of taking a plurality of EEG measurements, the method comprising:
    (a) providing a first and second plurality of electrode contact-points configured atop a support member, said first plurality in electrical communication with a first integrated circuit in electrical communication with, and in relative proximity to, said first contact-points;

(b) providing a second integrated circuit in electrical communication with, and in relative proximity to, said second contact points;

(c) severing said support member along a separation marking between said first plurality of contact-points in electrical communication with said first integrated circuit and said second plurality of contact-points in electrical communication with said second integrated circuit;

(d) locating that portion of said support member comprising said first plurality and said first integrated circuit for measuring analog EEG signals, having originated from within a patient, through said first plurality of electrode contact -points;

(e) prior to said measuring analog EEG signals, joining a quick-connect mechanism adapted to pull-apart upon a disturbance by said patient, located along a lead assembly between said first integrated circuit and a host processing unit; and (f) prior to transmitting information about said analog EEG signals to said host processing unit, converting said analog EEG signals into digital signals using circuitry of said first integrated circuit.

11. A method of taking a plurality of EEG measurements, the method comprising:

(a) providing a plurality of electrode contact-points configured atop a support member in electrical communication with an integrated circuit in relative proximity to said contact-points;

(b) severing said support member along a separation marking made between certain of said electrode contact-points and removing a portion of said support member containing at least one of said contact-points;

(c) locating a remaining portion of said support member comprising said integrated circuit, for measuring analog EEG signals, having originated from within a patient, through said electrode contact-points of said remaining portion; and (d) prior to transmitting information about said analog EEG signals to a host processing unit, converting said analog EEG signals into digital signals using circuitry of said integrated circuit.

12. The method of claim 11:

(a) further comprising, after said step of converting said analog EEG signals and prior to a step of electrically transmitting said digital signals from said integrated circuit, the steps of: filtering and processing said digital signals; and (b) wherein said step of electrically transmitting from said integrated circuit comprises: transmitting said digital signals from said integrated circuit through a lead assembly having wiring for a ground reference and for supplying power, and transmitting through a quick-connect mechanism to a recorder-processor unit worn by said patient, said quick-connect mechanism providing a connection adapted to pull-apart upon a disturbance by said patient, and thereafter on to a host processing unit.

13. The method of claim 11 further comprising, after said step of converting said analog EEG signals, a step of wirelessly transmitting electromagnetic waves comprising information about said digital signals, outwardly from an antenna wiring in electrical communication with said integrated circuit to a host processing unit.

* * * * *